(12) United States Patent
Singleton et al.

(10) Patent No.: US 9,392,789 B2
(45) Date of Patent: Jul. 19, 2016

(54) COMPOSITIONS OF DIBROMOMALONAMIDE AND THEIR USE AS BIOCIDES

(75) Inventors: Freddie L. Singleton, Vernon Hills, IL (US); Bei Yin, Buffalo Grove, IL (US); Janardhanan S. Rajan, Glenview, IL (US)

(73) Assignee: Dow Global Technologies LLC, Midland, MI (US)

(*) Notice: Subject to any disclaimer, the term of this patent is extended or adjusted under 35 U.S.C. 154(b) by 1045 days.

(21) Appl. No.: 13/388,696

(22) PCT Filed: Sep. 27, 2010

(86) PCT No.: PCT/US2010/050347
§ 371 (c)(1),
(2), (4) Date: Feb. 3, 2012

(87) PCT Pub. No.: WO2011/041252
PCT Pub. Date: Apr. 7, 2011

(65) Prior Publication Data
US 2012/0177745 A1    Jul. 12, 2012

Related U.S. Application Data

(60) Provisional application No. 61/246,713, filed on Sep. 29, 2009.

(51) Int. Cl.
| | | |
|---|---|---|
| *A01N 37/18* | (2006.01) | |
| *A01N 59/00* | (2006.01) | |
| *A01N 33/14* | (2006.01) | |
| *A01N 43/50* | (2006.01) | |
| *A01N 43/64* | (2006.01) | |

(52) U.S. Cl.
CPC ............. *A01N 37/18* (2013.01); *A01N 33/14* (2013.01); *A01N 43/50* (2013.01); *A01N 43/64* (2013.01); *A01N 59/00* (2013.01)

(58) Field of Classification Search
None
See application file for complete search history.

(56) References Cited

U.S. PATENT DOCUMENTS

| | | | |
|---|---|---|---|
| 4,163,795 | A | 8/1979 | Burk |
| 4,241,080 | A | 12/1980 | Burk |
| 4,800,082 | A | 1/1989 | Karbowski et al. |
| 4,959,157 | A | 9/1990 | Karbowski |
| 5,494,588 | A | 2/1996 | LaZonby |
| 2004/0035803 | A1 | 2/2004 | Cronan et al. |
| 2004/0261196 | A1 | 12/2004 | Ghosh et al. |
| 2009/0117202 | A1 | 5/2009 | Feldman et al. |

FOREIGN PATENT DOCUMENTS

| | | |
|---|---|---|
| EP | 0285209 A2 | 10/1988 |
| JP | 10-101511 | 4/1998 |
| WO | WO 2007096885 A2 * | 8/2007 |

OTHER PUBLICATIONS

Rice, E. W. 2003. Disinfection:Chlorine, Monochloramine, and Chlorine Dioxide. Encyclopedia of Environmental Microbiology.* vol. 2: Swimming Pools, Spas and Similar Recreational-water Environments, Chapter 5, Managing Water and Air Quality (2000), pp. 5-1-5-23.*

* cited by examiner

*Primary Examiner* — Abigail Fisher
*Assistant Examiner* — Frank Choi
(74) *Attorney, Agent, or Firm* — Tifani M. Edwards

(57) ABSTRACT

The application describes synergistic microbicidal compositions comprising: 2,2-dibromomalonamide and an oxidizing biocide selected from the group consisting of: monochloramine, bromochlorodimethylhydantoin, hypobromite ion or hypobromous acid, hydrogen peroxide, dichloroisocyanurate, trichloroisocyanurate and chlorine dioxide and a method for controlling microorganism growth in an aqueous or water-containing system.

4 Claims, No Drawings

COMPOSITIONS OF DIBROMOMALONAMIDE AND THEIR USE AS BIOCIDES

CROSS-REFERENCE TO RELATED APPLICATIONS

This application claims the benefit of U.S. Provisional Application Ser. No. 61/246,713, filed Sep. 29, 2009, which is incorporated herein by reference in its entirety.

This application is a 35 USC §371 national phase filing PCT/US2010/050347 filed Sep. 27, 2010, which claims the benefit of U.S Application No. 61/246,713, filed Sep. 29, 2009.

FIELD OF THE INVENTION

The invention relates to biocidal compositions and methods of their use for the control of microorganisms in aqueous and water-containing systems. The compositions comprise 2,2-dibromomalonamide and an oxidizing biocide.

BACKGROUND OF THE INVENTION

Water systems provide fertile breeding grounds for algae, bacteria, viruses, and fungi some of which can be pathogenic. Such microorganism contamination can create a variety of problems, including aesthetic unpleasantries such as slimy green water, serious health risks such as fungal, bacterial, or viral infections, and mechanical problems including plugging, corrosion of equipment, and reduction of heat transfer.

Biocides are commonly used to disinfect and control the growth of microorganisms in aqueous and water containing systems. However, not all biocides are effective against a wide range of microorganisms and/or temperatures, and some are incompatible with other chemical treatment additives. In addition, some biocides do not provide microbial control over long enough time periods.

While some of these shortcomings can be overcome through use of larger amounts of the biocide, this option creates its own problems, including increased cost, increased waste, and increased likelihood that the biocide will interfere with the desirable properties of the treated medium. In addition, even with use of larger amounts of the biocide, many commercial biocidal compounds cannot provide effective control due to weak activity against certain types of microorganisms or resistance of the microorganisms to those compounds.

It would be a significant advance in the art to provide biocide compositions for treatment of water systems that provide one or more of the following advantages: increased efficacy at lower concentrations, compatibility with physical conditions and other additives in the treated medium, effectiveness against a broad spectrum of microorganisms, and/or ability to provide both short term and long term control of microorganisms.

BRIEF SUMMARY OF THE INVENTION

In one aspect, the invention provides a biocidal composition. The composition is useful for controlling microorganisms in aqueous or water containing systems. The composition comprises: 2,2-dibromomalonamide and an oxidizing biocide selected from monochloramine, bromochlorodimethylhydantoin, hypobromite ion or hypobromous acid, hydrogen peroxide, dichloroisocyanurate, trichloroisocyanurate, and chlorine dioxide.

In a second aspect, the invention provides a method for controlling microorganisms in aqueous or water containing systems. The method comprises treating the system with an effective amount of a biocidal composition as described herein.

DETAILED DESCRIPTION OF THE INVENTION

As noted above, the invention provides a biocidal composition and methods of using it in the control of microorganisms. The composition comprises: 2,2-dibromomalonamide and an oxidizing biocide selected from monochloramine, bromochlorodimethylhydantoin, hypobromite ion or hypobromous acid, and hydrogen peroxide. It has surprisingly been discovered that combinations of 2,2-dibromomalonamide and the oxidizing biocide as described herein, at certain weight ratios, are synergistic when used for microorganism control in aqueous or water containing media. That is, the combined materials result in improved biocidal properties than would otherwise be expected based on their individual performance. The synergy permits reduced amounts of the materials to be used to achieve the desired biocidal performance, thus reducing problems caused by growth of microorganisms in industrial process waters while potentially reducing environmental impact and materials cost.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation. In some preferred embodiments, "control" and "controlling" mean inhibiting the growth or propagation of microorganisms. In further embodiments, "control" and "controlling" mean the killing of microorganisms.

The term "2,2-dibromomalonamide" refers to a compound represented by the following chemical formula:

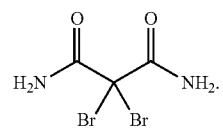

In some embodiments of the invention, the weight ratio of 2,2-dibromomalonamide to the oxidizing biocide is between about 100:1 and about 1:100, alternatively between about 40:1 and about 1:100, alternatively between about 32:1 and about 1:80.

In some embodiments, the composition of the invention comprises 2,2-dibromomalonamide and monochloramine. Monochloramine is readily prepared by those skilled in the art using well known techniques. For instance, it may be generated by mixing appropriate quantities of solutions of ammonium sulfate ($[NH_4]_2SO_4$) and hypochlorite ion, such as sodium hypochlorite. Monochloramine may, for instance, also be prepared by mixing ammonium bromide and hypochlorite ion. Hypochlorite ion may be in the form of commercial bleach (e.g., Clorox®). The product of mixing ammonium bromide and hypochlorite ion is sometimes considered to be "bromide-activated" monochloramine and other times simply monochloramine. All products of such mixing are encompassed by the term "monochloramine" as used in the invention, including bromide-activated monochloramine and simple monochloramine.

In some embodiments, the weight ratio of 2,2-dibromomalonamide to monochloramine is between about 100:1 and about 1:20, alternatively between about 70:1 and about 1:10, alternatively about 40:1 and about 1:5, alternatively between about 32:1 and about 1:4, or alternatively between about 32:1 and about 1:2. In some embodiments, the weight ratio is between about 16:1 and about 1:4.

In a still further embodiment, the composition of the invention comprises 2,2-dibromomalonamide and bromochlorodimethylhydantoin. Bromochlorodimethylhydantoin is commercially available.

In some embodiments, the weight ratio of 2,2-dibromomalonamide to bromochlorodimethylhydantoin is between about 20:1 and about 1:100, alternatively between about 10:1 and about 1:70, alternatively between about 5:1 and about 1:20, or alternatively between about 4:1 and about 1:16.

In another embodiment, the composition of the invention comprises 2,2-dibromomalonamide and hypobromous acid or hypobromous ion. Hypobromous acid and hypobromite ion are commercially available or can be readily by those skilled in the art (e.g., hypobromous acid can be generated by dissolving bromine in excess of water).

In some embodiments, the weight ratio of 2,2-dibromomalonamide to hypobromous acid or hypobromite ion is between about 20:1 and about 1:100, alternatively between about 10:1 and about 1:70, alternatively between about 5:1 and about 1:40, or alternatively between about 4:1 and about 1:32.

In a further embodiment, the composition of the invention comprises 2,2-dibromomalonamide and hydrogen peroxide. Solutions of hydrogen peroxide in water are commercially available.

In some embodiments, the weight ratio of 2,2-dibromomalonamide to hydrogen peroxide is between about 50:1 and about 1:100, alternatively between about 30:1 and about 1:80, alternatively between about 1:10 and about 1:80, or alternatively between about 1:20 and about 1:80.

In some embodiments, the oxidizing biocide is dichloroisocyanurate and the weight ratio of 2,2-dibromomalonamide to dichloroisocyanurate is between about 100:1 and about 1:20, alternatively between about 70:1 and about 1:10, alternatively about 40:1 and about 1:5, alternatively between about 32:1 and about 1:1.

In some embodiments, the oxidizing biocide is trichloroisocyanurate and the weight ratio of 2,2-dibromomalonamide to trichloroisocyanurate is between about 100:1 and about 1:20, alternatively between about 70:1 and about 1:10, alternatively about 40:1 and about 1:5, alternatively between about 16:1 and about 1:4.

In some embodiments, the oxidizing biocide is chlorine dioxide and the weight ratio of 2,2-dibromomalonamide to chlorine dioxide is between about 50:1 and about 1:50, alternatively between about 20:1 and about 1:20, alternatively about 16:1 and about 1:16.

Various of the oxidizing biocides described herein may be electrolytically generated.

The composition of the invention is useful for controlling microorganisms in a variety of aqueous and water containing systems. Examples of such systems include, but are not limited to, paints and coatings, aqueous emulsions, latexes, adhesives, inks, pigment dispersions, household and industrial cleaners, detergents, dish detergents, mineral slurries polymer emulsions, caulks and adhesives, tape joint compounds, disinfectants, sanitizers, metalworking fluids, construction products, personal care products, textile fluids such as spin finishes, industrial process water (e.g. oilfield water, pulp and paper water, cooling water), oilfield functional fluids such as drilling muds and fracturing fluids, fuels, air washers, wastewater, ballast water, filtration systems, and swimming pool and spa water. Preferred aqueous systems are metal working fluids, personal care, household and industrial cleaners, industrial process water, and paints and coatings. Particularly preferred are industrial process water, paints and coatings, metal working fluids, and textile fluids such as spin finishes.

A person of ordinary skill in the art can readily determine, without undue experimentation, the effective amount of the composition that should be used in any particular application to provide microorganism control. By way of illustration, a suitable actives concentration (total for both 2,2-dibromomalonamide and an oxidizing biocide) is typically at least about 1 ppm, alternatively at least about 3 ppm, alternatively at least about 7 ppm, alternatively at least about 10 ppm, alternatively at least about 30 ppm, or alternatively at least about 100 ppm based on the total weight of the aqueous or water containing system. In some embodiments, a suitable upper limit for the actives concentration is about 1000 ppm, alternatively about 500 ppm, alternatively about 100 ppm, alternatively about 50 ppm, alternatively about 30 ppm, alternatively about 15 ppm, alternatively about 10 ppm, or alternatively about 7 ppm, based on the total weight of the aqueous or water containing system.

The components of the composition can be added to the aqueous or water containing system separately, or preblended prior to addition. A person of ordinary skill in the art can easily determine the appropriate method of addition. The composition can be used in the system with other additives such as, but not limited to, surfactants, ionic/nonionic polymers and scale and corrosion inhibitors, oxygen scavengers, and/or additional biocides.

The following examples are illustrative of the invention but are not intended to limit its scope. Unless otherwise indicated, the ratios, percentages, parts, and the like used herein are by weight.

EXAMPLES

The results provided in the Examples are generated using a growth inhibition assay. Details of each assay are provided below.

Growth Inhibition Assay. The growth inhibition assay used in the Examples measures inhibition of growth (or lack thereof) of a microbial consortium Inhibition of growth can be the result of killing of the cells (so no growth occurs), killing of a significant portion of the populations of cells so that regrowth requires a prolonged time, or inhibition of growth without killing (stasis). Regardless of the mechanism of action, the impact of a biocide (or combination of biocides) can be measured over time on the basis of an increase in the size of the community.

The assay measures the efficacy of one or more biocides at preventing growth of a consortium of bacteria in a dilute mineral salts medium. The medium contains (in mg/l) the following components: $FeCl_3.6H_2O$ (1); $CaCl_2.2H_2O$ (10); $MgSO_4.7H_2O$ (22.5); $(NH_4)_2SO_4$ (40); $KH_2PO_4$ (10); $K_2HPO_4$ (25.5); Yeast Extract (10); and glucose (100). After all components are added to deionized water, the pH of the medium is adjusted to 7.5. Following filter sterilization, aliquots are dispensed in 100 ul quantities to sterile microtiter plate wells. Dilutions of 2,2-dibromomalonamide ("DB-MAL") and/or "Biocide B" are then added to the microtiter plate. After preparing the combinations of actives as illustrated below, each well is inoculated with 100 µl of a cell suspension containing ca. $1 \times 10^6$ cells per milliliter of a mixture of *Pseudomonas aeruginosa*, *Klebsiella pneumoniae*, Staphylococcus aureus, and Bacillus subtilis. The final total volume of medium in each well is 300 µl. Once prepared as described herein, the concentration of each active ranges from 25 ppm to 0.195 ppm as illustrated in Table 1. The resulting matrix allows testing of eight concentrations of each active and 64 combinations of actives in the ratios (of actives).

TABLE 1

Template for microtiter plate-based synergy assay showing concentrations of each active.
Ratios are based on weight (ppm) of each active.

|  |  | DBMAL (ppm) | | | | | | | |
|---|---|---|---|---|---|---|---|---|---|
|  |  | 25.000 | 12.500 | 6.250 | 3.125 | 1.563 | 0.781 | 0.391 | 0.195 |
| Biocide B (ppm) | 25.000 | 1:1 | 1:2 | 1:4 | 1:8 | 1:16 | 1:32 | 1:64 | 1:128 |
|  | 12.500 | 2:1 | 1 | 1:2 | 1:4 | 1:8 | 1:16 | 1:32 | 1:64 |
|  | 6.250 | 4:1 | 2:1 | 1 | 1:2 | 1:4 | 1:8 | 1:16 | 1:32 |
|  | 3.125 | 8:1 | 4:1 | 2:1 | 1 | 1:2 | 1:4 | 1:8 | 1:16 |
|  | 1.563 | 16:1 | 8:1 | 4:1 | 2:1 | 1 | 1:2 | 1:4 | 1:8 |
|  | 0.781 | 32:1 | 16:1 | 8:1 | 4:1 | 2:1 | 1 | 1:2 | 1:4 |
|  | 0.391 | 64:1 | 32:1 | 16:1 | 8:1 | 4:1 | 2:1 | 1 | 1:2 |
|  | 0.195 | 128:1 | 64:1 | 32:1 | 16:1 | 8:1 | 4:1 | 2:1 | 1:1 |

Controls (not shown) contain the medium with no biocide added. After preparing the combinations of actives as illustrated above, each well is inoculated with 100 µl of a cell suspension containing ca. $1 \times 10^6$ cells per milliliter of a mixture of Pseudomonas aeruginosa, Klebsiella pneumoniae, Staphylococcus aureus, and Bacillus subtilis. The final total volume of medium in each well is 300 µl.

Immediately after the microtiter plates are prepared, the optical density (OD) readings for each well is measured at 580 nm and the plates are then incubated at 37° C. for 24 hr. After the incubation period, the plates are gently agitated before $OD_{580}$ values are collected. The $OD_{580}$ values at $T_0$ are subtracted from $T_{24}$ values to determine the total amount of growth (or lack thereof) that occurs. These values are used to calculate the percent inhibition of growth caused by the presence of each biocide and each of the 64 combinations. A 90% inhibition of growth is used as a threshold for calculating synergy index (SI) values with the following equation:

Synergy Index = $M_{DBMAL}/C_{DBMAL} + M_B/C_B$ where
$C_{DBMAL}$: Concentration of DBMAL required to inhibit ~90% of bacterial growth when used alone
$C_B$: Concentration of biocide (B) required to inhibit ~90% of bacterial growth when used alone.
$M_{DBMAL}$: Concentration of DBMAL required to inhibit ~90% of bacterial growth when used in combination with biocide (B).
$M_B$: Concentration of biocide (B) required to inhibit ~90% of bacterial growth when used in combination with DBMAL The SI values are interpreted as follows:
SI<1: Synergistic combination
SI=1: Additive combination
SI>1: Antagonistic combination In the Examples below, the amounts of biocides in the solution are measured in mg per liter of solution (mg/l). Since solution densities are approximately 1.00, the mg/l measurement corresponds to weight ppm. Both units may therefore be used interchangeably in the Examples.

Example 1

DBMAL and Monochloramine Prepared from Ammonium Sulfate and Bleach

Monochloramine ($NH_2Cl$) is generated by mixing appropriate quantities of solutions of ammonium sulfate ($[NH_4]_2SO_4$) and commercial bleach (Clorox®). Table 2 shows inhibition growth assay results for DBMAL, monochloramine ($NH_2Cl$), and combinations thereof. The results demonstrate that the $I_{90}$ values for $NH_2Cl$ and DBMAL are 1.56 mg/l and 12.5 mg/l, respectively (Table 2). Combinations of $NH_2Cl$ and DBMAL are very effective at preventing growth as illustrated by the results obtained with the combination of 0.78 mg/l $NH_2Cl$ and 0.19 mg/l DBMAL.

TABLE 2

Percent inhibition of growth in a species-defined microbial consortium by DBMAL and monochloramine ($NH_2Cl$) and alone and combinations of these actives after a 24-hour incubation period. Numbers represent percent inhibition of growth as measured by optical density measurements (580 nm) at time = 24 hours compared with time = 0 values.

| | Single Actives (mg/l) | | | | | Combinations of DBMAL and $NH_2Cl$ | | | | | | | |
|---|---|---|---|---|---|---|---|---|---|---|---|---|---|
| % Inhibition of growth in Untreated Control | DBMAL Concn. (mg/l) | % Inhibition of growth by DBMAL | $NH_2Cl$ Concn. (mg/l) | % Inhibition of growth $NH_2Cl$ | DBMAL Concn. (mg/l) | $NH_2Cl$ Concn. (mg/l) | | | | | | | |
| | | | | | | 25.0 | 12.5 | 6.25 | 3.13 | 1.56 | 0.78 | 0.39 | 0.19 |
| 10 | 25.0 | 98 | 25.0 | 95 | 25.0 | 98 | 97 | 94 | 53 | 100 | 100 | 100 | 73 |
| 2 | 12.5 | 100 | 12.5 | 97 | 12.5 | 95 | 96 | 91 | 100 | 100 | 100 | 100 | 100 |
| 5 | 6.25 | 9 | 6.25 | 94 | 6.25 | 97 | 92 | 98 | 94 | 100 | 100 | 100 | 0 |
| 0 | 3.13 | 17 | 3.13 | 96 | 3.13 | 98 | 100 | 89 | 67 | 100 | 100 | 0 | 0 |
| 0 | 1.56 | 9 | 1.56 | 97 | 1.56 | 99 | 100 | 100 | 100 | 100 | 100 | 0 | 0 |

TABLE 2-continued

Percent inhibition of growth in a species-defined microbial consortium by DBMAL and monochloramine (NH$_2$Cl) and alone and combinations of these actives after a 24-hour incubation period. Numbers represent percent inhibition of growth as measured by optical density measurements (580 nm) at time = 24 hours compared with time = 0 values.

| % Inhibition of growth in Untreated Control | Single Actives (mg/l) | | | | | Combinations of DBMAL and NH$_2$Cl | | | | | | | |
|---|---|---|---|---|---|---|---|---|---|---|---|---|---|
| | DBMAL Concn. (mg/l) | % Inhibition of growth by DBMAL | NH$_2$Cl Concn. (mg/l) | % Inhibition of growth NH$_2$Cl | DBMAL Concn. (mg/l) | NH$_2$Cl Concn. (mg/l) | | | | | | | |
| | | | | | | 25.0 | 12.5 | 6.25 | 3.13 | 1.56 | 0.78 | 0.39 | 0.19 |
| 6 | 0.78 | 22 | 0.78 | 2 | 0.78 | 100 | 100 | 100 | 100 | 100 | 100 | 0 | 0 |
| 0 | 0.39 | 4 | 0.39 | 0 | 0.39 | 99 | 97 | 88 | 89 | 100 | 100 | 0 | 0 |
| 2 | 0.19 | 11 | 0.19 | 4 | 0.19 | 99 | 100 | 100 | 100 | 100 | 100 | 0 | 0 |

Table 3 shows ratios of DBMAL and NH$_2$Cl found to be synergistic under the growth inhibition assay.

TABLE 3

| DBMAL Concn. (mg/l) | NH$_2$Cl Concn. (mg/l) | Ratio (DBMAL to NH$_2$Cl) | Synergy Index (SI) |
|---|---|---|---|
| 3.13 | 0.78 | 4:1 | 0.75 |
| 1.56 | 0.78 | 2:1 | 0.63 |
| 0.78 | 0.78 | 1:1 | 0.56 |
| 0.39 | 0.78 | 1:2 | 0.53 |
| 0.20 | 0.78 | 1:4 | 0.52 |
| 6.25 | 0.39 | 16:1 | 0.75 |

Example 3

DBMAL and Monochloramine Prepared from Ammonium Bromide/Hypochlorite

Monochloramine is prepared by mixing together appropriate quantities of ammonium bromide and hypochlorite.

Table 4 shows inhibition growth assay results for DBMAL, ammonium bromide/hypochlorite, and combinations thereof.

Table 5 shows ratios of DBMAL and ammonium bromide/hypochlorite found to be synergistic under the growth inhibition assay.

TABLE 5

| DBMAL Concn. (mg/l) | AmBr/hypo Concn. (mg/l) | Ratio (DBMAL to AmBr/hypo) | SI |
|---|---|---|---|
| 3.13 | 0.78 | 4:1 | 0.75 |
| 1.56 | 0.78 | 2:1 | 0.63 |
| 0.78 | 0.78 | 1:1 | 0.56 |
| 0.39 | 0.78 | 1:2 | 0.53 |
| 6.25 | 0.39 | 16:1 | 0.75 |
| 6.25 | 0.20 | 32:1 | 0.63 |

Example 4

DBMAL and BCDMH

Table 6 shows inhibition growth assay results for DBMAL, bromochlorodimethylhydantoin ("BCDMH"), and combinations thereof.

TABLE 4 percent inhibition of growth in a species-defined microbial consortium by DBMAL and/or ammonium bromide/hypochlorite after a 24-hour incubation period. Numbers represent percent inhibition of growth as measured by optical density measurements (580 nm) at time = 24 hours compared with time = 0 values.

| % Inhibition of growth in Untreated Control | Single Actives (mg/l) | | | | | Combinations of DBMAL and AmBr/Hypo | | | | | | | |
|---|---|---|---|---|---|---|---|---|---|---|---|---|---|
| | DBMAL Concn. (mg/l) | % Inhibition of growth by DBMAL | AmBr/Hypo Concn. (mg/l) | % Inhibition of growth by AmBr/Hypo | DBMAL Concn. (mg/l) | AmBr/Hypo Concn. (mg/l) | | | | | | | |
| | | | | | | 25.0 | 12.5 | 6.25 | 3.13 | 1.56 | 0.78 | 0.39 | 0.19 |
| 0 | 25.0 | 100 | 25.0 | 89 | 25.0 | 100 | 100 | 97 | 100 | 100 | 100 | 100 | 100 |
| 0 | 12.5 | 100 | 12.5 | 99 | 12.5 | 99 | 100 | 100 | 100 | 100 | 100 | 100 | 100 |
| 38 | 6.25 | 0 | 6.25 | 99 | 6.25 | 99 | 97 | 99 | 100 | 100 | 100 | 100 | 98 |
| 0 | 3.13 | 0 | 3.13 | 100 | 3.13 | 98 | 100 | 100 | 0 | 100 | 100 | 0 | 0 |
| 0 | 1.56 | 5 | 1.56 | 99 | 1.56 | 99 | 100 | 100 | 100 | 100 | 100 | 0 | 0 |
| 0 | 0.78 | 0 | 0.78 | 78 | 0.78 | 99 | 100 | 100 | 100 | 100 | 100 | 0 | 0 |
| 0 | 0.39 | 0 | 0.39 | 0 | 0.39 | 99 | 100 | 100 | 100 | 100 | 100 | 0 | 0 |
| 0 | 0.19 | 0 | 0.19 | 0 | 0.19 | 99 | 100 | 100 | 100 | 100 | 0 | 0 | 0 |

TABLE 6

Percent inhibition of growth in a species-defined microbial consortium by DBMAL and/or BCDMH after a 24-hour incubation period. Numbers represent percent inhibition of growth as measured by optical density measurements (580 nm) at time = 24 hours compared with time = 0 values.

| % Inhibition of growth in Untreated Control | Single Actives (mg/l) | | | | Combinations of DBMAL and BCDMH | | | | | | | |
|---|---|---|---|---|---|---|---|---|---|---|---|---|
| | DBMAL Concn. (mg/l) | % Inhibition of growth by DBMAL | BCDMH Concn. (mg/l) | % Inhibition of growth by BCDMH | DBMAL Concn. (mg/l) | BCDMH Concn. (mg/l) | | | | | | |
| | | | | | | 25.0 | 12.5 | 6.25 | 3.13 | 1.56 | 0.78 | 0.39 | 0.19 |
| 0 | 25.0 | 100 | 25.0 | 99 | 25.0 | 98 | 100 | 100 | 100 | 100 | 100 | 100 | 100 |
| 0 | 12.5 | 100 | 12.5 | 98 | 12.5 | 100 | 100 | 100 | 100 | 100 | 100 | 100 | 98 |
| 3 | 6.25 | 19 | 6.25 | 100 | 6.25 | 100 | 100 | 100 | 100 | 100 | 0 | 0 | 0 |
| 2 | 3.13 | 6 | 3.13 | 2 | 3.13 | 100 | 100 | 100 | 100 | 0 | 0 | 0 | 0 |
| 0 | 1.56 | 4 | 1.56 | 0 | 1.56 | 100 | 99 | 100 | 100 | 0 | 0 | 0 | 0 |
| 5 | 0.78 | 14 | 0.78 | 5 | 0.78 | 98 | 100 | 100 | 100 | 0 | 0 | 0 | 0 |
| 0 | 0.39 | 0 | 0.39 | 0 | 0.39 | 100 | 100 | 100 | 100 | 0 | 0 | 0 | 0 |
| 0 | 0.19 | 0 | 0.19 | 0 | 0.19 | 99 | 100 | 99 | 100 | 0 | 0 | 0 | 0 |

Table 7 shows concentrations of DBMAL and BCDMH that are found to be synergistic using the growth inhibition assay.

TABLE 7

| DBMAL Concn. (mg/l) | BCDMH Concn. (mg/l) | Ratio (DBMAL to BCDMH) | Synergy Index (SI) |
|---|---|---|---|
| 3.125 | 3.125 | 1:1 | 0.75 |
| 1.56 | 3.125 | 1:2 | 0.63 |
| 0.78 | 3.125 | 1:4 | 0.56 |
| 0.39 | 3.125 | 1:8 | 0.53 |
| 0.195 | 3.125 | 1:16 | 0.52 |
| 6.25 | 1.56 | 4:1 | 0.75 |

Example 5

DBMAL and Hypobromous Acid

Table 8 shows inhibition growth assay results for DBMAL, hypobromous acid ("HOBr"), and combinations thereof. In this example, HOBr is generated immediately before use by mixing equimolar amounts of sodium hypochlorite (NaOCl) and sodium bromide (NaBr).

Table 9 shows concentrations of DBMAL and HOBr found to be synergistic using the growth inhibition assay.

TABLE 9

| DBMAL Concn. (mg/l) | HOBr Concn. (mg/l) | Ratio (DBMAL:HOBr) | Synergy Index (SI) |
|---|---|---|---|
| 6.25 | 3.13 | 2:1 | 0.75 |
| 6.25 | 1.56 | 4:1 | 0.63 |
| 3.13 | 6.25 | 1:2 | 0.75 |
| 3.13 | 3.13 | 1:1 | 0.50 |
| 3.13 | 1.56 | 2:1 | 0.38 |
| 1.56 | 6.25 | 1:4 | 0.62 |
| 1.56 | 3.13 | 1:2 | 0.37 |
| 1.56 | 1.56 | 1:1 | 0.25 |
| 0.78 | 6.25 | 1:8 | 0.56 |
| 0.78 | 3.13 | 1:4 | 0.31 |
| 0.78 | 1.56 | 1:2 | 0.19 |
| 0.39 | 6.25 | 1:16 | 0.53 |
| 0.39 | 3.13 | 1:8 | 0.28 |
| 0.39 | 1.56 | 1:4 | 0.16 |
| 0.20 | 6.25 | 1:32 | 0.52 |
| 0.20 | 3.13 | 1:16 | 0.27 |
| 0.20 | 1.56 | 1:8 | 0.14 |

TABLE 8

Percent inhibition of growth in a species-defined microbial consortium by DBMAL and/or HOBr after a 24-hour incubation period. Numbers represent percent inhibition of growth as measured by optical density measurements (580 nm) at time = 24 hours compared with time = 0 values.

| % Inhibition of growth in Untreated Control | Single Actives (mg/l) | | | | Combinations of DBMAL and HOBr | | | | | | | |
|---|---|---|---|---|---|---|---|---|---|---|---|---|
| | DBMAL Concn. (mg/l) | % Inhibition of growth by DBMAL | HOBr Concn. (mg/l) | % Inhibition of growth by HOBr | DBMAL Concn. (mg/l) | HOBr Concn. (mg/l) | | | | | | |
| | | | | | | 25.0 | 12.5 | 6.25 | 3.13 | 1.56 | 0.78 | 0.39 | 0.19 |
| 5 | 25.0 | 100 | 25.0 | 100 | 25.0 | 99 | 100 | 99 | 98 | 100 | 98 | 100 | 100 |
| 3 | 12.5 | 99 | 12.5 | 99 | 12.5 | 100 | 99 | 100 | 100 | 100 | 100 | 99 | 0 |
| 1 | 6.25 | 0 | 6.25 | 57 | 6.25 | 100 | 100 | 100 | 100 | 100 | 0 | 0 | 0 |
| 0 | 3.13 | 1 | 3.13 | 22 | 3.13 | 100 | 100 | 100 | 100 | 100 | 0 | 0 | 0 |
| 0 | 1.56 | 0 | 1.56 | 0 | 1.56 | 100 | 100 | 98 | 100 | 100 | 0 | 0 | 0 |
| 3 | 0.78 | 0 | 0.78 | 0 | 0.78 | 99 | 100 | 100 | 100 | 100 | 0 | 0 | 0 |
| 6 | 0.39 | 5 | 0.39 | 0 | 0.39 | 100 | 100 | 100 | 100 | 100 | 0 | 0 | 0 |
| 0 | 0.19 | 1 | 0.19 | 0 | 0.19 | 100 | 100 | 99 | 100 | 100 | 0 | 0 | 0 |

Example 6

DBMAL and Hydrogen Peroxide

Table 10 shows inhibition growth assay results for DBMAL, hydrogen peroxide ($H_2O_2$), and combinations thereof.

TABLE 10

Percent inhibition of growth in a species-defined microbial consortium by DBMAL and/or $H_2O_2$ after a 24-hour incubation period. Numbers represent percent inhibition of growth as measured by optical density measurements (580 nm) at time = 24 hours compared with time = 0 values.

| % Inhibition of growth in Untreated Control | Single Actives (mg/l) | | | | Combinations of DBMAL and $H_2O_2$ | | | | | | | | |
|---|---|---|---|---|---|---|---|---|---|---|---|---|---|
| | DBMAL Concn. (mg/l) | % Inhibition of growth by DBMAL | $H_2O_2$ Concn. (mg/l) | % Inhibition of growth by $H_2O_2$ | DBMAL Concn. (mg/l) | $H_2O_2$ Concn. (mg/l) | | | | | | | |
| | | | | | | 1000 | 500 | 250.00 | 125 | 62.5 | 31.25 | 15.625 | 7.813 |
| 0 | 25.0 | 100 | 1,000 | 89 | 25.0 | 100 | 99 | 100 | 100 | 100 | 100 | 100 | 100 |
| 3 | 12.5 | 92 | 500 | 100 | 12.5 | 100 | 100 | 100 | 100 | 100 | 100 | 98 | 96 |
| 0 | 6.25 | 9 | 250 | 1 | 6.25 | 100 | 100 | 100 | 100 | 0 | 0 | 0 | 0 |
| 2 | 3.13 | 15 | 125 | 6 | 3.13 | 100 | 100 | 100 | 0 | 0 | 0 | 0 | 0 |
| 4 | 1.56 | 12 | 62.5 | 12 | 1.56 | 100 | 100 | 69 | 0 | 0 | 0 | 0 | 0 |
| 0 | 0.78 | 2 | 31.25 | 0 | 0.78 | 100 | 18 | 50 | 0 | 0 | 0 | 0 | 0 |
| 9 | 0.39 | 8 | 15.63 | 2 | 0.39 | 100 | 100 | 0 | 0 | 0 | 0 | 0 | 0 |
| 2 | 0.19 | 6 | 7.81 | 5 | 0.19 | 100 | 49 | 22 | 0 | 0 | 0 | 0 | 0 |

Table 11 shows the one concentration of DBMAL and $H_2O_2$ found to be synergistic using the growth inhibition assay.

TABLE 11

| DBMAL Concn. (mg/l) | $H_2O_2$ Concn. (mg/l) | Ratio (DBMAL to $H_2O_2$) | Synergy Index (SI) |
|---|---|---|---|
| 3.125 | 250 | 1:80 | 0.75 |
| 6.25 | 125 | 1:20 | 0.5 |

Example 7

DBMAL and Dichloroisocyanurate

Table 12 shows inhibition growth assay results for DBMAL, dichloroisocyanurate, and combinations thereof.

Table 13 shows the concentrations of DBMAL and DCI found to be synergistic using the growth inhibition assay.

TABLE 13

| DBMAL Concn. (mg/l) | DCI Concn. (mg/l) | Ratio (DBMAL to $H_2O_2$) | Synergy Index (SI) |
|---|---|---|---|
| 3.13 | 0.78 | 4:1 | 0.75 |
| 1.56 | 0.78 | 2:1 | 0.63 |
| 0.78 | 0.78 | 1:1 | 0.56 |
| 6.25 | 0.39 | 16:1 | 0.75 |
| 6.25 | 0.20 | 32:1 | 0.63 |

Example 8

DBMAL and Trichloroisocyanurate

Table 14 shows inhibition growth assay results for DBMAL, trichloroisocyanurate ("TCI"), and combinations thereof.

TABLE 12

Percent inhibition of growth in a species-defined microbial consortium by DBMAL and/or DCI after a 24-hour incubation period. Numbers represent percent inhibition of growth as measured by optical density measurements (580 nm) at time = 24 hours compared with time = 0 values.

| % Inhibition of growth in Untreated Control | Single Actives (mg/l) | | | | Combinations of DBMAL and DCI | | | | | | | | |
|---|---|---|---|---|---|---|---|---|---|---|---|---|---|
| | DBMAL Concn. (mg/l) | % Inhibition of growth by DBMAL | DCI Concn. (mg/l) | % Inhibition of growth by DCI | DBMAL Concn. (mg/l) | DCI Concn. (mg/l) | | | | | | | |
| | | | | | | 25.0 | 12.5 | 6.25 | 3.125 | 1.563 | 0.781 | 0.392 | 0.195 |
| 7 | 25.0 | 100 | 25.0 | 100 | 25.0 | 99 | 99 | 99 | 99 | 98 | 100 | 99 | 100 |
| 3 | 12.5 | 100 | 12.5 | 100 | 12.5 | 100 | d | 98 | 99 | 96 | 100 | 100 | 99 |
| 3 | 6.25 | 6 | 6.25 | 97 | 6.25 | 98 | 100 | 100 | 100 | 100 | 100 | 92 | 98 |
| 0 | 3.13 | 0 | 3.13 | 100 | 3.13 | 100 | 98 | 100 | 100 | 100 | 100 | 0 | 0 |
| 3 | 1.56 | 0 | 1.56 | 98 | 1.56 | 100 | 85 | 100 | 100 | 100 | 100 | 0 | 0 |
| 0 | 0.78 | 0 | 0.78 | 0 | 0.78 | 97 | 100 | 100 | 100 | 100 | 93 | 19 | 0 |
| 0 | 0.39 | 2 | 0.39 | 0 | 0.39 | 98 | 100 | 100 | 98 | 100 | 0 | 0 | 0 |
| 6 | 0.19 | 7 | 0.19 | 0 | 0.19 | 100 | 49 | 22 | 0 | 0 | 0 | 0 | 0 |

TABLE 14

Percent inhibition of growth in a species-defined microbial consortium by DBMAL and/or TCI after a 24-hour incubation period. Numbers represent percent inhibition of growth as measured by optical density measurements (580 nm) at time = 24 hours compared with time = 0 values

| % Inhibition of growth in Untreated Control | Single Actives (mg/l) | | | | Combinations of DBMAL and TCI | | | | | | | | |
|---|---|---|---|---|---|---|---|---|---|---|---|---|---|
| | DBMAL Concn. (mg/l) | % Inhibition of growth by DBMAL | TCI Concn. (mg/l) | % Inhibition of growth by TCI | DBMAL Concn. (mg/l) | TCI Concn. (mg/l) | | | | | | | |
| | | | | | | 25.0 | 12.5 | 6.25 | 3.125 | 1.563 | 0.781 | 0.392 | 0.195 |
| 0 | 25.0 | 100 | 25 | 94 | 25.0 | 92 | 100 | 96 | 100 | 99 | 100 | 99 | 100 |
| 5 | 12.5 | 100 | 12.5 | 97 | 12.5 | 85 | 98 | 96 | 98 | 100 | 100 | 100 | 100 |
| 0 | 6.25 | 13 | 6.25 | 99 | 6.25 | 98 | 100 | 100 | 100 | 100 | 100 | 100 | 0 |
| 3 | 3.13 | 0 | 3.13 | 96 | 3.13 | 92 | 98 | 98 | 99 | 100 | 100 | 100 | 0 |
| 1 | 1.56 | 0 | 1.56 | 97 | 1.56 | 100 | 99 | 100 | 100 | 100 | 100 | 0 | 0 |
| 0 | 0.78 | 0 | 0.78 | 0 | 0.78 | 100 | 96 | 99 | 97 | 100 | 100 | 0 | 0 |
| 11 | 0.39 | 0 | 0.39 | 0 | 0.39 | 100 | 97 | 96 | 100 | 100 | 100 | 0 | 0 |
| 0 | 0.19 | 0 | 0.19 | 0 | 0.19 | 100 | 96 | 88 | 99 | 99 | 100 | 0 | 0 |

Table 15 shows the concentrations of DBMAL and TCI found to be synergistic using the growth inhibition assay.

TABLE 15

| DBMAL Concn. (mg/l) | TCI Concn. (mg/l) | Ratio (DBMAL to TCI) | Synergy Index (SI) |
|---|---|---|---|
| 3.13 | 0.78 | 4:1 | 0.75 |
| 1.56 | 0.78 | 2:1 | 0.63 |
| 0.78 | 0.78 | 1:1 | 0.56 |
| 0.39 | 0.78 | 1:2 | 0.53 |
| 0.20 | 0.78 | 1:4 | 0.52 |
| 6.25 | 0.39 | 16:1 | 0.75 |
| 3.13 | 0.39 | 8:1 | 0.50 |

Example 8

DBMAL and Chlorine Dioxide

Table 16 shows inhibition growth assay results for DBMAL, chlorine dioxide (ClO$_2$), and combinations thereof.

Table 17 shows the concentrations of DBMAL and ClO$_2$ found to be synergistic using the growth inhibition assay.

TABLE 17

| DBMAL Concn. (mg/l) | ClO$_2$ Concn. (mg/l) | Ratio (DBMAL to ClO$_2$) | Synergy Index (SI) |
|---|---|---|---|
| 3.13 | 3.13 | 1:1 | 0.75 |
| 1.56 | 3.13 | 1:2 | 0.63 |
| 0.78 | 3.13 | 1:4 | 0.56 |
| 0.39 | 3.13 | 1:8 | 0.53 |
| 0.20 | 3.13 | 1:16 | 0.52 |
| 6.25 | 1.56 | 4:1 | 0.75 |
| 3.13 | 1.56 | 2:1 | 0.50 |
| 1.56 | 1.56 | 1:1 | 0.38 |
| 6.25 | 0.78 | 8:1 | 0.63 |
| 6.25 | 0.39 | 16:1 | 0.56 |

While the invention has been described above according to its preferred embodiments, it can be modified within the spirit and scope of this disclosure. This application is therefore

TABLE 16

Percent inhibition of growth in a species-defined microbial consortium by DBMAL and/or chlorine dioxide (ClO$_2$) after a 24-hour incubation period. Numbers represent percent inhibition of growth as measured by optical density measurements (580 nm) at time = 24 hours compared with time = 0 values

| % Inhibition of growth in Untreated Control | Single Actives (mg/l) | | | | Combinations of DBMAL and ClO$_2$ | | | | | | | | |
|---|---|---|---|---|---|---|---|---|---|---|---|---|---|
| | DBMAL Concn. (mg/l) | % Inhibition of growth by DBMAL | ClO$_2$ Concn. (mg/l) | % Inhibition of growth by ClO$_2$ | DBMAL Concn. (mg/l) | ClO$_2$ Concn. (mg/l) | | | | | | | |
| | | | | | | 25.0 | 12.5 | 6.25 | 3.13 | 1.56 | 0.78 | 0.39 | 0.19 |
| 0 | 25.0 | 100 | 25 | 98 | 25.0 | 100 | 99 | 99 | 100 | 100 | 100 | 100 | 100 |
| 0 | 12.5 | 100 | 12.5 | 100 | 12.5 | 100 | 100 | 100 | 100 | 100 | 100 | 100 | 100 |
| 5 | 6.25 | 20 | 6.25 | 99 | 6.25 | 99 | 100 | 100 | 100 | 100 | 96 | 84 | 19 |
| 4 | 3.13 | 11 | 3.13 | 75 | 3.13 | 88 | 100 | 99 | 100 | 90 | 0 | 13 | 0 |
| 1 | 1.56 | 5 | 1.56 | 63 | 1.56 | 96 | 100 | 100 | 100 | 94 | 36 | 6 | 0 |
| 0 | 0.78 | 1 | 0.78 | 35 | 0.78 | 100 | 99 | 100 | 57 | 64 | 42 | 0 | 0 |
| 4 | 0.39 | 8 | 0.39 | 26 | 0.39 | 100 | 100 | 100 | 100 | 59 | 28 | 0 | 0 |
| 3 | 0.19 | 9 | 0.19 | 12 | 0.19 | 100 | 100 | 85 | 100 | 61 | 36 | 0 | 0 |

What is claimed is:

1. A synergistic biocidal composition comprising: synergistically effective amounts of 2,2-dibromomalonamide and an oxidizing biocide selected from the group consisting of monochloramine, bromochlorodimethylhydantoin, hypobromite ion or hypobromous acid, hydrogen peroxide, dichloroisocyanurate, trichloroisocyanurate, and chlorine dioxide;
   wherein when the oxidizing biocide is monochloramine, the weight ratio of 2,2-dibromomalonamide to monochloramine is between 32:1 and 1:4;
   wherein when the oxidizing biocide is bromochlorodimethylhydantoin the weight ratio of the 2,2dibromomalonamide to the bromochlorodimethylhydantoin is between 4:1 and 1:16;
   wherein when the oxidizing biocide is hypobromite ion or hypobromous acid the weight ratio of the 2,2dibromomalonamide to the hypobromite ion or hypobromous acid is between 4:1 and 1:32;
   wherein when the oxidizing biocide is hydrogen peroxide the weight ratio of the 2,2-dibromomalonamide to the hydrogen peroxide is between 1:20 and 1:80;
   wherein when the oxidizing biocide is dichloroisocyanurate the weight ratio of the 2,2-dibromomalonamide to the dichloroisocyanurate is between 32:1 and 1:1;
   wherein when the oxidizing biocide is trichloroisocyanurate the weight ratio of the 2,2-dibromomalonamide to trichloroisocyanurate is between 16:1 and 1:4;
   wherein when the oxidizing biocide is chlorine dioxide the weight ratio of the 2,2-dibromomalonamide to the chlorine dioxide is between 16:1 and 1:16.

2. A composition according to claim 1 which is: paint, coating, aqueous emulsion, latex, adhesive, ink, pigment dispersion, household or industrial cleaner, detergent, dish detergent, mineral slurry polymer emulsion, caulk, adhesive, tape joint compound, disinfectant, sanitizer, metalworking fluid, construction product, personal care product, textile fluid, spin finish, industrial process water, oilfield functional fluid, fuel, air washer, wastewater, ballast water, filtration systems, swimming pool or spa water.

3. A method for controlling microorganism growth in an aqueous or water-containing system, the method comprising treating the aqueous or water-containing system with an effective amount of a composition according to claim 1.

4. A method according to claim 3 wherein the aqueous or water-containing system is paint, coating, aqueous emulsion, latex, adhesive, ink, pigment dispersion, household or industrial cleaner, detergent, dish detergent, mineral slurry polymer emulsion, caulk, adhesive, tape joint compound, disinfectant, sanitizer, metalworking fluid, construction product, personal care product, textile fluid, spin finish, industrial process water, oilfield functional fluid, fuel, air washer, wastewater, ballast water, filtration system, swimming pool or spa water.

* * * * *